United States Patent
Lary

(10) Patent No.: US 7,244,243 B2
(45) Date of Patent: Jul. 17, 2007

(54) CATHETER FOR TREATMENT OF SEVERE PULMONARY EMBOLI

(76) Inventor: Banning Gray Lary, 6371 SW. 87th Ter., Miami, FL (US) 33143

( * ) Notice: Subject to any disclaimer, the term of this patent is extended or adjusted under 35 U.S.C. 154(b) by 0 days.

(21) Appl. No.: 11/200,766

(22) Filed: Aug. 8, 2005

(65) Prior Publication Data

US 2006/0206053 A1    Sep. 14, 2006

Related U.S. Application Data

(60) Provisional application No. 60/661,528, filed on Mar. 10, 2005, provisional application No. 60/690,177, filed on Jun. 9, 2005.

(51) Int. Cl.
*A61M 29/00*    (2006.01)

(52) U.S. Cl. ............... 604/96.01; 604/103.01

(58) Field of Classification Search ................ 604/158, 604/159, 539, 96.01, 103.01, 103.02, 513, 604/103.03, 103.06, 103.07, 101.01, 101.02, 604/101.03, 101.04, 101.05; 606/200
See application file for complete search history.

(56) References Cited

U.S. PATENT DOCUMENTS

| | | | |
|---|---|---|---|
| 3,996,938 A | 12/1976 | Clark, III | |
| 4,575,371 A | 3/1986 | Nordqvist et al. | |
| 4,577,631 A | 3/1986 | Kreamer | |
| 4,747,406 A | 5/1988 | Nash | |
| 4,923,462 A | 5/1990 | Stevens | |
| 5,011,488 A | 4/1991 | Ginsburg | |
| 5,242,389 A * | 9/1993 | Schrader et al. | 604/513 |
| 5,279,546 A | 1/1994 | Mische et al. | |
| 5,370,653 A | 12/1994 | Cragg | |
| 5,425,723 A | 6/1995 | Wang | |
| 5,527,292 A | 6/1996 | Adams et al. | |
| 5,569,204 A | 10/1996 | Cramer | |
| 5,569,275 A | 10/1996 | Kotula et al. | |
| 5,624,396 A | 4/1997 | McNamara et al. | |
| 5,695,457 A * | 12/1997 | St. Goar et al. | 604/4.01 |
| 5,713,848 A | 2/1998 | Dubrul et al. | |
| 5,795,331 A * | 8/1998 | Cragg et al. | 604/103.01 |
| 5,833,650 A | 11/1998 | Imran | |
| 6,013,085 A | 1/2000 | Howard | |
| 6,063,069 A | 5/2000 | Cragg et al. | |
| 6,295,989 B1 | 10/2001 | Connors, III | |
| 6,485,500 B1 * | 11/2002 | Kokish et al. | 606/194 |
| 6,852,097 B1 | 2/2005 | Fulton, III | |
| 6,908,474 B2 | 6/2005 | Hogendijk et al. | |
| 2002/0026145 A1 * | 2/2002 | Bagaoisan et al. | 604/96.01 |

\* cited by examiner

*Primary Examiner*—Nicholas Lucchesi
*Assistant Examiner*—Theodore J. Stigell
(74) *Attorney, Agent, or Firm*—McHale & Slavin, P.A.

(57) ABSTRACT

A catheter system for treating pulmonary emboli has an multi-channel access port for establishing and maintaining communication with the vascular system and provide guidance for endovascular catheterization. One catheter may traverse the port and extend through the heart to the pulmonary arteries to inject lysing agents, contrast media, medicaments and to remove blood clots. Another catheter may traverse the port and extend through the vena cava to other parts of the venous tree to supply the same agents and to remove blood clots there. A third catheter may telescope over the treatment catheter through the vena cava and occlude the affected vein. Gas pervious tubules on the third catheter provide oxygen enrichment of the venous blood.

3 Claims, 4 Drawing Sheets

CATHETER FOR TREATMENT OF SEVERE PULMONARY EMBOLI

RELATED APPLICATIONS

Priority of filing date is claimed from U.S. Provisional Application 60/661,528 filed Mar. 10, 2005 and 60/690,177 filed Jun. 9, 2005.

FIELD OF THE INVENTION

This invention relates to the apparatus and methods of endovascular treatment of blood clots obstructing passageways in the circulatory system.

BACKGROUND OF THE INVENTION

Thromboembolism is a serious and life threatening problem. The emboli can be sudden and massive and at other times they may be small and multiple. They can be any size and happen at any time.

When blood clots form in the venous circulation of the body they may move or embolize to the lungs. The clots typically embolize from the veins of the legs, pelvis, or inferior vena cava to the right heart cavities and thence into the pulmonary arteries. This results in right heart failure and decreased blood flow through the lungs with subsequent decreased oxygenation of the lungs, heart and the rest of the body. When clots enter the pulmonary arteries obstruction and spasm of the different arteries of the lung occurs which further decreases blood flow and gaseous exchange through the lung tissue resulting in pulmonary edema. All of these factors decrease the oxygen in the blood in the left heart. The oxygenated blood supplied by the coronary arteries to the musculature of both the left and right heart is insufficient for proper contractions of the muscle which further decreases the entire oxygenated blood flow to the rest of the body.

This malady is common and has many causes, among them are prolonged inactivity such as bed rest, dehydration, extensive surgery or protracted disease and many others in which the blood of the inferior peripheral major circulatory system may coagulate to varying degrees with permanent drainage problems.

DESCRIPTION OF THE PRIOR ART

The prior art contains numerous treatments for this malady, including anticoagulants, antibiotics, peripheral constrictive bandages and surgical attempts at removal of the emboli from the pulmonary artery. The surgical attempts may rely on catherterization of the affected vessels and application of chemical or mechanical agents or both to disintegrate the clot. For example, U.S. Pat. No. 6,852,097 to Fulton III discloses using mechanical agitation and chemical agents to destroy blood clots.

SUMMARY OF THE INVENTION

What is lacking in the art is a method and apparatus for maintaining blood oxygenation levels in the circulation system until the emboli can be eliminated and normalized blood flow re-established.

Accordingly, it is a primary objective of the instant invention to provide a catheter system for removing clots and oxygenating the blood.

It is a further objective of the instant invention to prevent venous clots from approaching the heart.

It is yet another objective of the instant invention provide a catheter with an exchange membrane for introducing oxygen into the circulation system.

It is a still further objective of the instant invention to provide a port for introducing the catheter system into the circulation system.

It is another objective of the instant invention to provide cumulative treatment of other portions of the circulation system.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
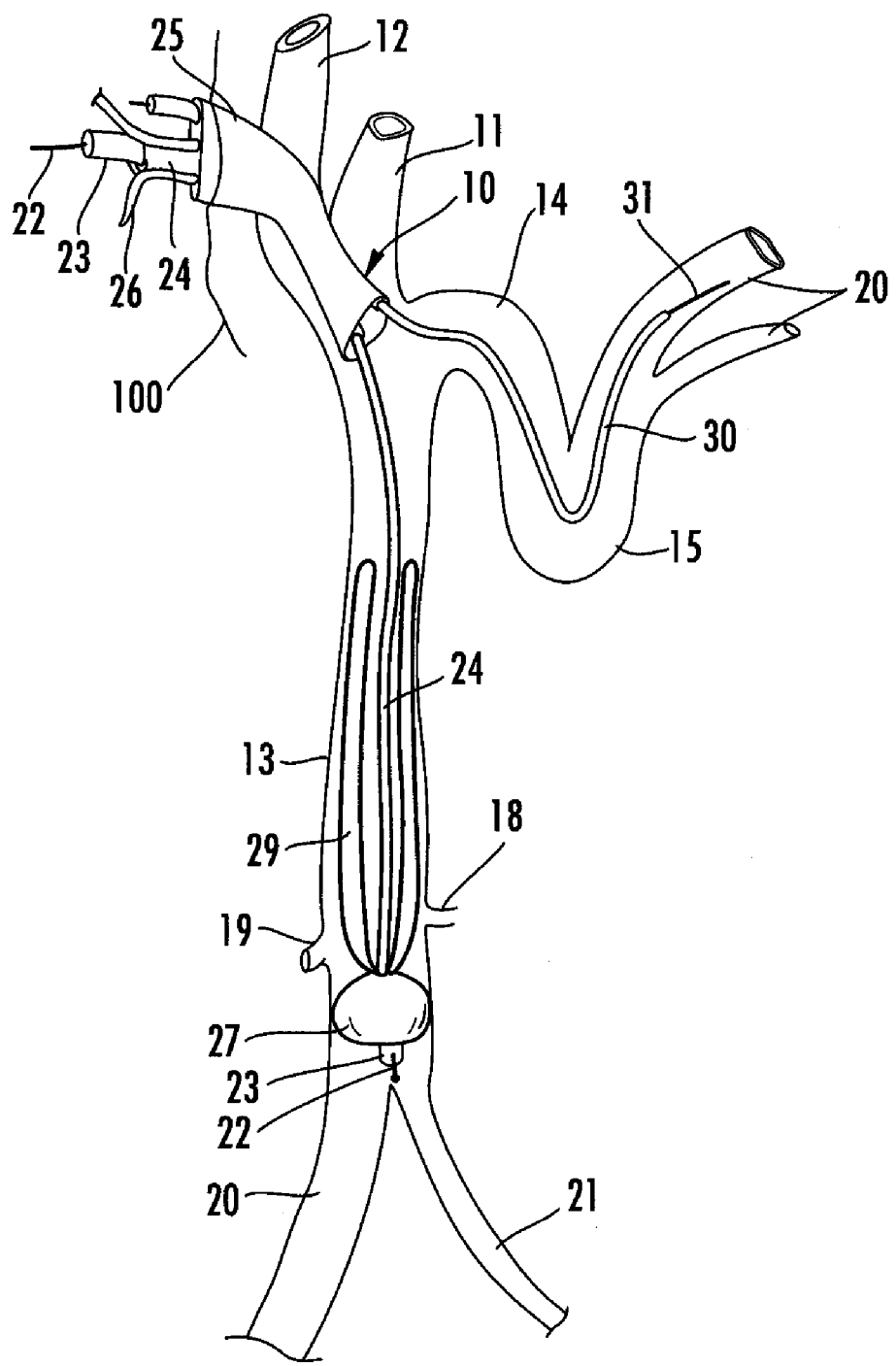
FIG. 1 is a simplified cross section of the circulatory system with a catheter system of this invention inserted.
Figure 2:
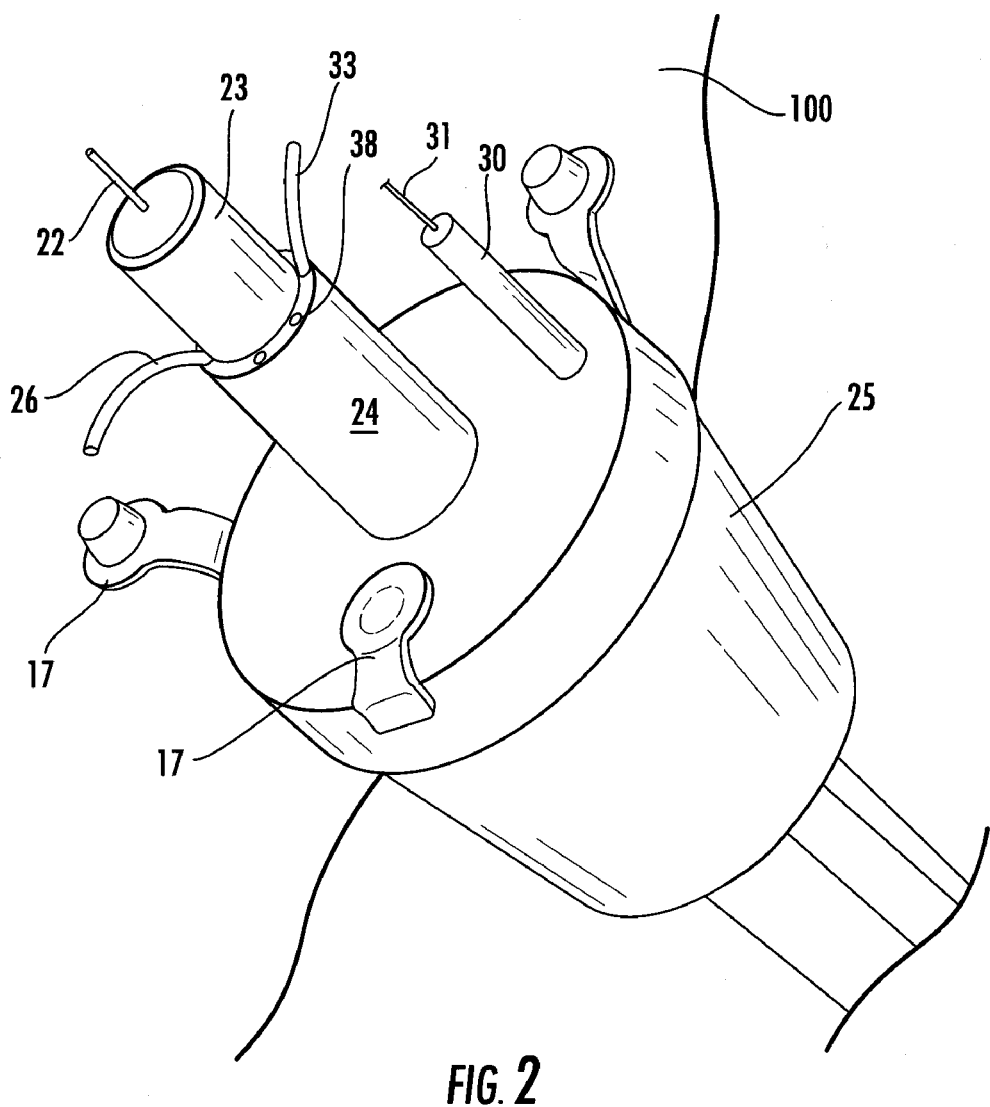
FIG. 2 is a perspective of the port of this invention and the proximal end of the catheter system.

When the diagnosis of acute severe pulmonary embolism is established, the apparatus 10 is applied as rapidly as possible. Using a local anesthetic a small incision is made over the external jugular vein 12, the internal jugular vein 11 or similar vein. The catheter system 10, shown in FIG. 1, has an access port 25, in the nature of a cannula, which extends through the incision in the skin 100 and underlying tissue to penetrate into the venous system. The port 25 has several lumen through which other components of the system may be deployed. Each lumen has an occlusive device 17, as shown in FIG. 2, for closing each channel when it is not in use. The lumen act as a guide for initial insertion of the catheters that are included in the system 10. A guide wire 22 is passed through the port 25 into the external jugular 12 inferior into the vena cava 13 to the distal venous tree. Radiographic utilities are used where possible for visualization of the placement of the guide wire. Contrast media may be used to demonstrate the location of the clot(s).

Figure 4:
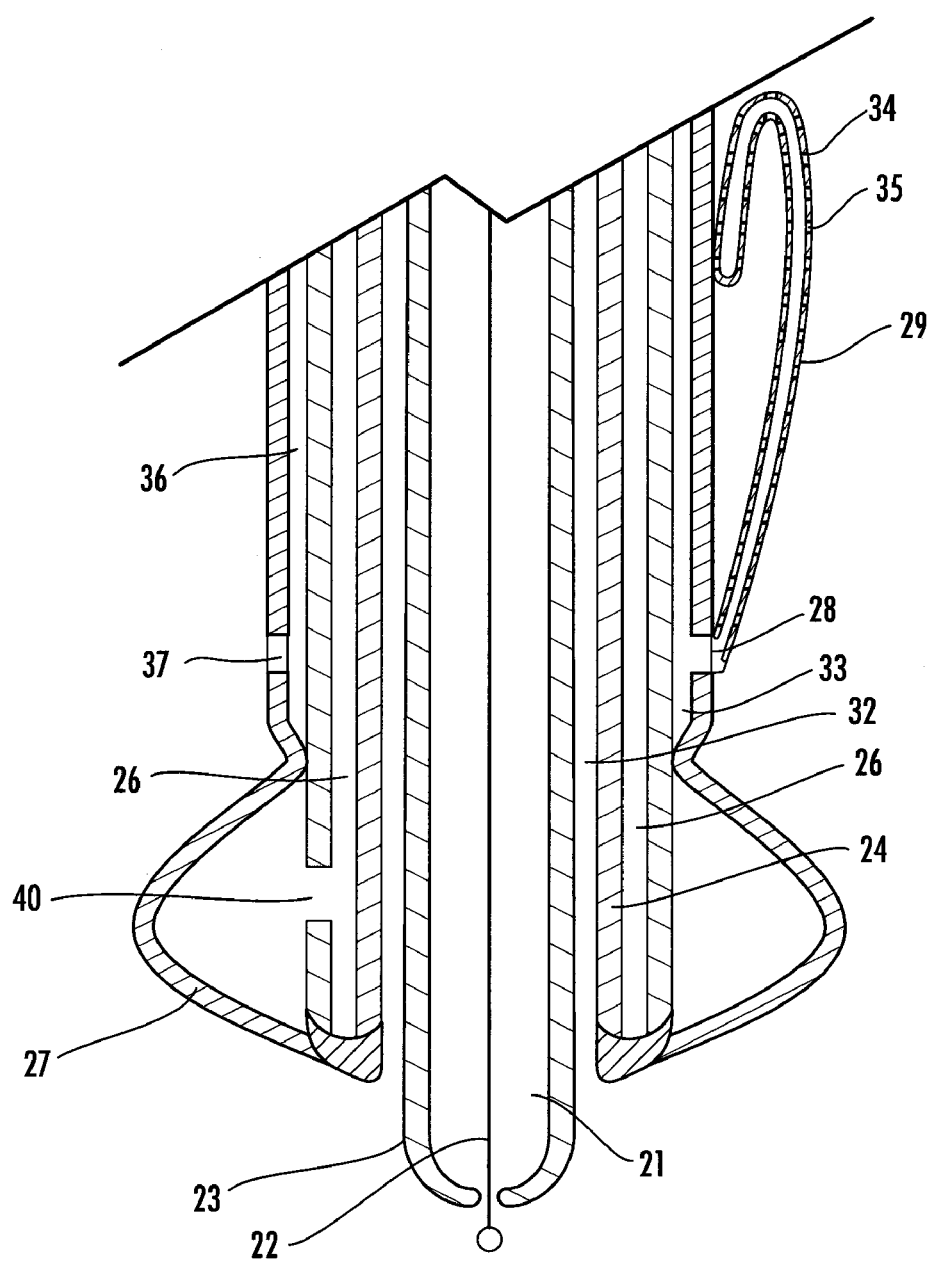
FIG. 4 is a cross section of the distal end of the catheter of this invention.

Over the guide wire 22 is passed a catheter 23 that will be subsequently used to remove the clot(s) by administration of lytic agents or maceration conducted through lumen 21, shown in FIG. 4. The catheter 23 can be multi-lumen to provide simultaneous suction for removal of debris during reduction of the clot(s).

A placement catheter 24 with a central lumen 32 is telescoped over catheter 23 through the lumen in port 25 and to the area in the venous tree proximal to the clot(s). The placement catheter has an extendible balloon 27 surrounding the distal end. When the placement catheter is inserted as far as possible, as determined by radiography or other means, the balloon 27 is distended by fluid directed through lumen 26 and aperture 40. The distended balloon occludes the vena cava below the renal arteries. As shown in FIG. 1, the distended balloon is distal to the renal arteries 18 and 19.

The inflated balloon prevents further emboli and decreases central venous hypertension to immediately improve right heart failure.

An additional catheter 30 is passed through port 25 over previously placed guide wire 31 to enter the right auricle 14, the right ventricle 15 and the pulmonary arteries 20. This catheter 30 may have multi-lumen for maceration, lysis and suction removal of pulmonary clot(s).

The deployment and use of catheter 23 and catheter 30 may be simultaneous or sequential but form part of the treatment regimen.

As soon as practical, oxygen is supplied to the venous blood proximal to the distended balloon to improve the systemic blood oxygenation in the vena cava. Several tubules 29 are attached proximal to the balloon 27 through connections 28 communicating with several lumen 33 in catheter 24. The tubules have a convoluted shape to increase the surface area exposed to the blood flow. Oxygen is supplied through the lumen 33 and connections 28 to the tubules 29. The walls 34 of the tubules 29 are pervious to gaseous oxygen by pores 35. The tubules are inflated with minimal pressure to sustain an oxygen rich environment.

The tubules 29 permit the circulation of gaseous oxygen through the walls resulting in an exchange of oxygen and carbon dioxide with an increase of oxygen saturation of the venous blood returning to the heart through the right auricle, right ventricle, the pulmonary arteries and their branches. This, in turn, would decrease pulmonary edema and permit greater oxygenation through the normal alveolae into the blood that enters the left ventricle and subsequently to the coronary arteries which improves the cardiac contractions and increases the delivery of increased oxygenated blood to the rest of the body.

Figure 3:
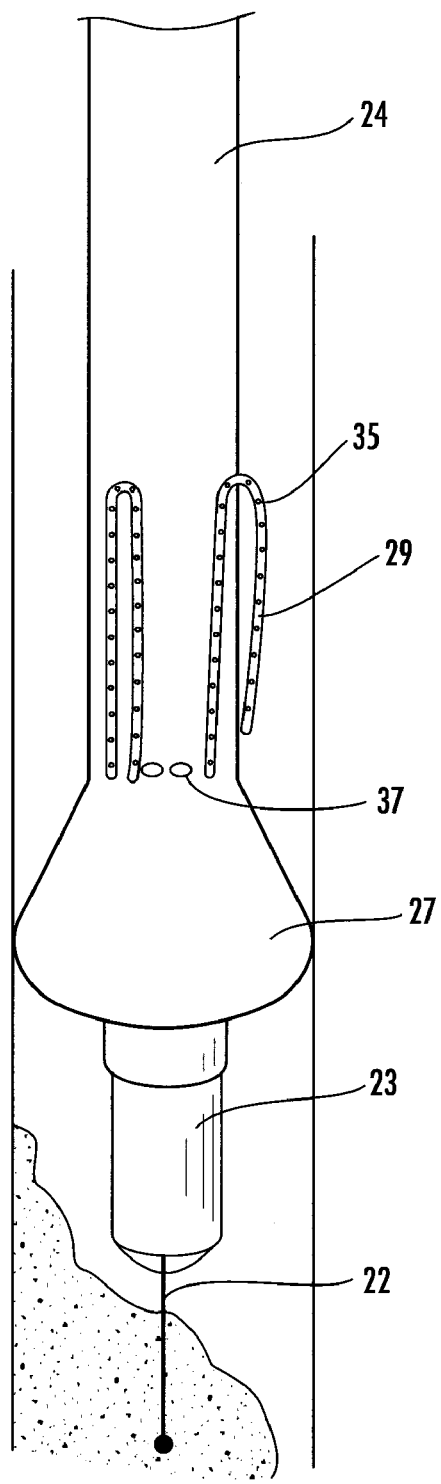
FIG. 3 is a perspective of the distal end of the catheter system of this invention.

The catheter 24 also has another set of lumen 36 which are open at both the distal and proximal ends. One distal opening 37 is shown in FIG. 4 and one proximal opening 38 is shown in FIG. 2. These lumen serve to vent the excess oxygen and carbon dioxide developed by gas exchange around the tubules. Multiple tubules may be employed for oxygen delivery and several others for suction to remove the carbon dioxide and some oxygen, see FIG. 3.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

I claim:

1. A catheter system for endovascular procedures comprising; a port for accessing the vascular system from outside a patient, said port having an external surface with a tubular extension for placement in the vascular system, said port having a plurality of channels extending from said external surface through said tubular extension, a first catheter having a proximal end and a distal end and being disposed in one of said plurality of channels, said first catheter having a length sufficient to allow said distal end to traverse said patient's heart when said proximal end extends outside of the patient, a second catheter having a proximal end and a distal end and being disposed in a second of said plurality of channels, said second catheter having a length sufficient to allow said distal end to traverse said patient's vena cava and extend into the venous tree when said proximal end extends outside of the patient, a third catheter constructed and arranged to telescope about said second catheter, said third catheter having a proximal end and a distal end, an inflatable balloon surrounding said distal end of said third catheter, said third catheter having an inflation fluid supply lumen extending therethrough and in fluid communication with said inflatable balloon and said outside of said patient for supplying inflation fluid to said inflatable balloon, said third catheter also having at least one gas pervious tubule attached to an exterior portion of said third catheter proximal to said inflatable balloon, said first catheter having a first lumen extending therethrough for transporting treatment agents, said second catheter having a second lumen extending therethrough for transporting treatment agents, said third catheter having a third lumen extending therethrough for transporting oxygen enriched gas to said at least one gas pervious tubule, whereby endovascular procedures may be executed in different parts of the vascular system.

2. A catheter system of claim 1 comprising a plurality of occlusive devices attached to said external surface of said port, said occlusive devices adapted to temporarily close said plurality of channels not being used.

3. A catheter system of claim 1 comprising at comprising at least one vent lumen in said third catheter extending from said proximal end to said distal end whereby excess products of endovascular gas exchange are released to atmosphere.

* * * * *